United States Patent

Kanbe et al.

[11] 4,225,708
[45] Sep. 30, 1980

[54] 2-SULFAMOYL-5-SULFAMIDO-1-NAPHTHOLS

[75] Inventors: Masaru Kanbe; Kazumasa Watanabe; Morito Uemura; Jiro Takahashi; Ryuichiro Kobayashi; Tatsuhiko Kobayashi, all of Hino, Japan

[73] Assignee: Konishiroku Photo Industry Co., Ltd., Tokyo, Japan

[21] Appl. No.: 68,518

[22] Filed: Aug. 22, 1979

[30] Foreign Application Priority Data

Aug. 31, 1978 [JP]  Japan ................................ 53-106464

[51] Int. Cl.² .................... C07D 245/12; C07C 143/78
[52] U.S. Cl. .................................... 544/159; 260/165; 260/198; 260/556 N; 546/206
[58] Field of Search ................... 260/556 N; 546/206; 544/159

[56] References Cited

PUBLICATIONS

Hinshaw et al., "Chem. Abstracts", vol. 87, (1977), No. 103,370w.

*Primary Examiner*—Alan L. Rotman
*Assistant Examiner*—R. W. Ramsuer
*Attorney, Agent, or Firm*—Frishauf, Holtz, Goodman & Woodward

[57] ABSTRACT

2-Sulfamoyl-5-sulfamido-1-naphthols represented by the formula:

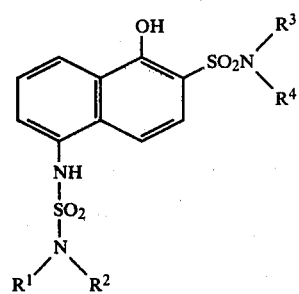

wherein $R^1$, $R^2$, $R^3$ and $R^4$ can be the same or different and each represent a hydrogen atom, a straight-chain alkyl group, a branched alkyl group or a cycloalkyl group; or $R^1$ and $R^2$ can be connected with each other, together with the nitrogen atom, to form a

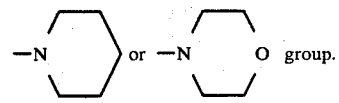 group.

12 Claims, No Drawings

2-SULFAMOYL-5-SULFAMIDO-1-NAPHTHOLS

This invention relates to a 2-sulfamoyl-5-sulfamido-1-naphthol compound which is novel and is useful as an intermediate for a new dye.

An object of the present invention is to provide a novel compound useful as an intermediate, which is stable against both an acid and an alkali, for an azo dye having excellent hue, dyeing ability and stability against light.

The compound according to this invention is represented by formula [I]:

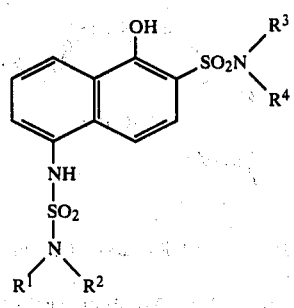

wherein $R^1$, $R^2$, $R^3$ and $R^4$, which can be same or different, independently represent a hydrogen atom, a straight-chain alkyl group having 1 to 6 carbon atoms, a branched alkyl group having 3 to 6 carbon atoms or a cycloalkyl group having 5 to 6 carbon atoms; or $R^1$ and $R^2$ may be connected with each other, together with the nitrogen atom, to form a

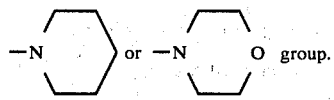

In formula [I], the straight-chain alkyl group having 1 to 6 carbon atoms includes, for example, methyl, ethyl, n-propyl, n-butyl, n-pentyl and n-hexyl group. The branched alkyl group having 3 to 6 carbon atoms includes, for example, isopropyl, sec-butyl, isobutyl, tert-butyl, isopentyl, tert-pentyl and isohexyl. The cycloalkyl group having 5 to 6 carbon atoms may include, for example, cyclopentyl and cyclohexyl which have a substituent therein.

$R^1$ and $R^2$ preferably represent a hydrogen atom, a straight-chain alkyl group having 1 to 6 carbon atoms or a branched alkyl group having 3 to 6 carbon atoms, or $R^1$ and $R^2$ may be connected with each other, together with the nitrogen atom, to form a

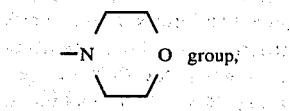

and more preferably $R^1$ and $R^2$ independently represent a hydrogen atom or a methyl group, or $R^1$ and $R^2$ may be connected with each other, together with the nitrogen atom, to form a

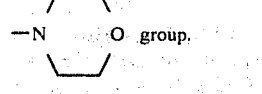

Preferably $R^1$ and $R^2$ are the same and more preferably both $R^1$ and $R^2$ are methyl groups.

$R^3$ and $R^4$ preferably represent a hydrogen atom, a straight-chain alkyl group having 1 to 6 carbon atoms or a branched alkyl group having 3 to 6 carbon atoms, and more preferably they independently represent a hydrogen atom, a straight-chain alkyl group having 1 to 4 carbon atoms or a branched alkyl group having 3 to 4 carbon atoms.

Preferably the total sum of carbon atoms in both $R^3$ and $R^4$ is 4 to 6 and more preferably $R^3$ is a hydrogen atom and $R^4$ is a tert-butyl group, or both $R^3$ and $R^4$ are isopropyl groups.

The compound of this invention may be prepared according to the following reaction formulae:

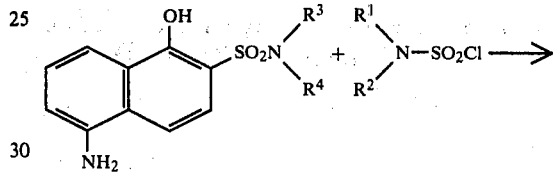

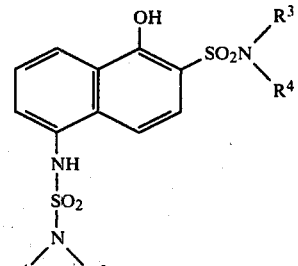

wherein $R^1$, $R^2$, $R^3$ and $R^4$ have the same meanings as defined above.

Thus, the compound having formula [I] may be prepared by reacting a 2-sulfamoyl-1-naphthol having formula [II] with an aminosulfonyl chloride having formula [III] in the presence of a tertiary amine.

More specifically, the compound of formula [I] may be prepared, for example, by dissolving a 2-sulfamoyl-1-naphthol of formula [II] in ten times as much dry pyridine as the compound (II), subsequently adding approximately equimolar amount, based on the compound (II), of an aminosulfonyl chloride (III) with stirring under cooling and then stirring the resulting mixture further for 1 to 20 hours at room temperature to around 40° C. After completion of the reaction, the reaction product may be obtained by pouring the reaction mixture into 3 to 5 times as much an ice-water which has been made acidic with hydrochloric acid and collecting the thus precipitated crystals by filtration, which are then washed sufficiently with water and dried. If desired, the product thus yielded may further be purified by recrystallization or by other suitable method.

Thus prepared 2-sulfamoyl-5-sulfamido-naphthols according to this invention are novel compounds, being valuable as an intermediate for azo dyes, i.e., a coupler and being useful for preparing various kinds of azo dyes according to known methods.

The azo dye prepared by using the coupler of this invention is represented by general formula [IV];

[IV]

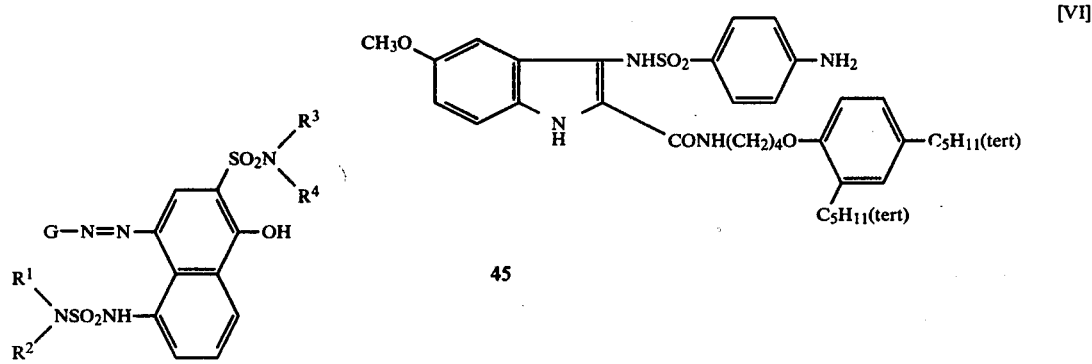

wherein G represents a benzenoid moiety or a heterocyclic ring moiety which may generally be seen in azo dyes, such as a group of an aromatic or heterocyclic azo component; and $R^1$, $R^2$, $R^3$ and $R^4$ have the same meanings as defined above, and can give various clear dyes belonging to a red through blue group dye.

Such a dye may be prepared by diazotizing an amine represented by formula G—$NH_2$ and coupling the resulting diazonium salt with the compound according to this invention.

Such amines having the formula G—$NH_2$ and diazonium salts prepared from the amines have been described, for example, in Hiroshi Horiguchi, pages 114–124 (1968), "Gohsei-senryo (Synthetic Dye)" and Yutaka Hosoda, pages 113–120 (1963) "Shin-senryo-kagaku (New Dye Chemistry)".

By selecting a compound G—$NH_2$, there may be prepared general dyes such as disperse dyes, direct cotton dyes, acid dyes and so on as well as dye image-forming compounds which are valuable for special uses. The dye image-forming compounds may be used for a color diffusion transfer photography and has been described on pages 336–372 of "The Theory of the Photographic Process, the fourth edition" by T. H. James. For instance, the following compound represented by general formula [V] may be prepared.

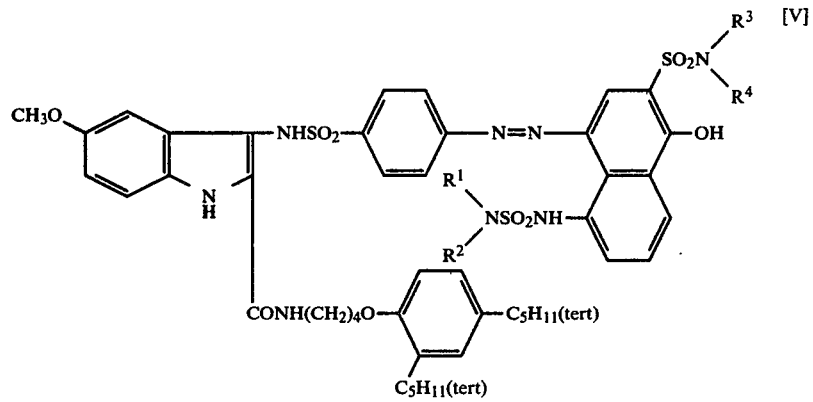

wherein $R^1$, $R^2$, $R^3$ and $R^4$ have the same meanings as defined above.

The preparation of the dye image-forming compound represented by formula [V] is carried out in the same manner as in the preparation of general dyes unless the compound G—$NH_2$ has a relatively complex structural formula.

Thus, it may be prepared by diazotizing the amine compound represented by following formula [VI]:

[VI]

and coupling the resulting diazonium salt with 2-sulfamoyl-5-sulfamido-1-naphthol.

Compounds of the present invention are capable of starting a coupling reaction either under acidic or alkaline conditions and the novel dyes which can be obtained from these intermediates of the invention have improved hue and stability against acid, alkali and light and as a photographic dye e.g., for color diffusion transfer process, in particular, these dyes have excellent adsorbing ability to a mordant, stability over a wide pH range, of their chemical structures and colors.

Examples of the compounds according to this invention will be shown below.

Compound 1.

-continued

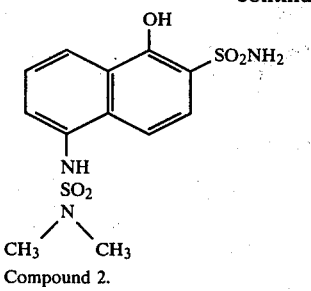

Compound 2.    m.p. 171° C.

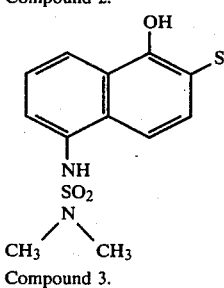

Compound 3.    m.p. 159°–160° C.

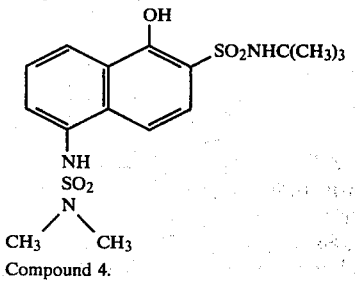

Compound 4.    m.p. 102°–103° C.

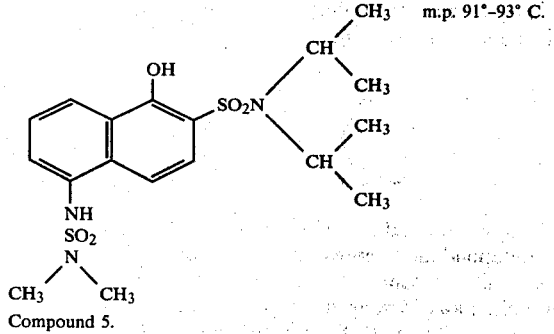

Compound 5.    m.p. 91°–93° C.

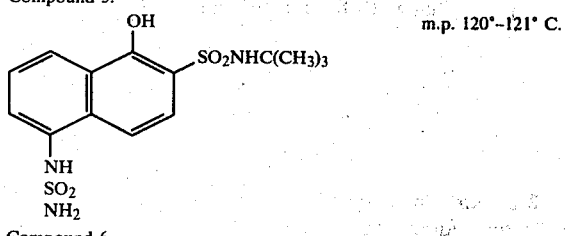

Compound 6.    m.p. 120°–121° C.

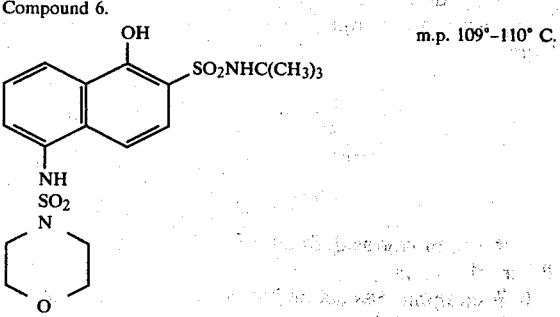

m.p. 109°–110° C.

| Compound | Elementary analysis | | | | | |
|---|---|---|---|---|---|---|
| | Calcd. | | | Found | | |
| No. | C % | H % | N % | C % | H % | N % |
| 1 | 41.73 | 4.38 | 12.17 | 41.57 | 4.36 | 12.04 |
| 2 | 43.44 | 4.77 | 11.69 | 43.36 | 4.65 | 11.82 |
| 3 | 47.87 | 5.77 | 10.47 | 48.03 | 5.82 | 10.40 |
| 4 | 50.33 | 6.34 | 9.78 | 50.27 | 6.29 | 9.74 |
| 5 | 45.03 | 5.13 | 11.25 | 45.15 | 5.23 | 11.08 |
| 6 | 48.74 | 5.68 | 9.47 | 48.56 | 5.60 | 9.33 |

Preparation of the compound according to this invention and a novel dye prepared from the compound will further be explained in more detail by way of the following Examples.

EXAMPLE 1

Preparation of Compound 3(2-tert-butylsulfamoyl-5-N,N-dimethylsulfamido-1-naphthol)

To a mixture of 98 g. of 5-amino-2-tert-butylsulfamoyl-1-naphthol and 800 ml. of dry pyridine were added dropwise 92 g. of N,N-dimethylaminosulfonyl chloride under ice-cooling with stirring. After the mixture was stirred at room temperature for 16 hours, the reaction mixture was poured into 6 l. of a mixture of ice and 6 l. of 2 N aqueous hydrochloric acid so that a solid was precipitated. The solid thus precipitated was collected on a filter funnel and washed with water. The solid thus obtained was dissolved in an 8% aqueous sodium hydroxide and insoluble substances were filtered.

Upon pouring the filtrate into a mixture of ice and 2.5 l. of 2 N aqueous hydrochloric acid, a solid was precipitated. The solid thus obtained was collected on a filter funnel, washed sufficiently with water and dried. The yield was 100 g. (79% of the theoretical amount). Confirmation of the structure of the compound was carried out by its Elementary analysis, Infrared (IR) spectrum and Nuclear Magnetic Resonance (N.M.R.) spectrum.

EXAMPLE 2

Preparation of an acid dye [sodium salt of 2-tert-butylsulfamoyl-4-(4-sulfophenyl)azo-5-N,N-dimethylsulfamido-1-naphthol] by using Compound 3 as a coupler In 100 ml. of water was dispersed 19 g. of sulfanilic acid, and 5.9 g. of anhydrous sodium carbonate was added thereto to dissolve the sulfanilic acid.

To the mixture was added, with stirring under ice-cooling, 50 ml. of an aqueous solution containing 8.2 g. of sodium nitrite, and then 120 ml. of a diluted aqueous hydrochloric acid was added dropwise thereto over 15 minutes. Thereafter, the mixture was stirred for 45 hours, during which the temperature was kept at 5° to 10° C.

Separately, 40.1 g. of 2-tert-butylsulfamoyl-5-N,N-dimethylsulfamido-1-naphthol was dissolved in 300 ml. of an 8% aqueous sodium hydroxide, and 1 ml. of n-amyl alcohol was added thereto as an antifoaming agent. The diazonium salt solution prepared previously was added with stirring under ice-cooling and the resulting mixture was stirred at room temperature for 2 hours. To the reaction mixture was added 120 g. of sodium chloride, and to salt out the produced dye which was then collected by filtration with a filter, washed with a 20% aqueous sodium chloride and then dried. The yield was 56 g. (92% of the theoretical amount). Confirmation of the structure was carried out by its IR spectrum and Elementary analysis.

Melting point: not less than 300° C.

Wave length at which maximum absorbance was observed in aqueous solution (λmax.) 548 nm.

Half width: 95 nm.

EXAMPLE 3

Preparation of a dye image-forming compound having the following structural formula

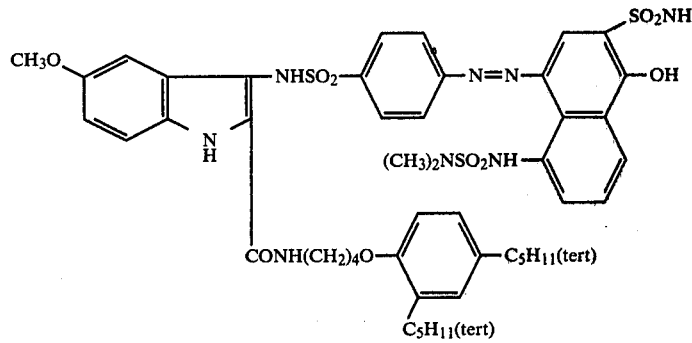

by using Compound 3 as a coupler

In 350 ml. of acetone was dissolved 20.5 g. of the amine compound having formula [VI], and 16 ml. of concentrated hydrochloric acid was added thereto. With introducing argon gas thereinto, 80 ml. of an aqueous solution containing 2.32 g. of sodium nitrite was added dropwise thereto with stirring, under ice-cooling over 10 minutes to prepare a diazonium salt solution.

To the diazonium salt solution was added dropwise with stirring under ice-cooling over 30 minutes a coupler solution prepared by dissolving 12.1 g. of Compound 3 in a solvent mixture of 60 ml. of pyridine and 240 ml. of acetic acid, and the resulting mixture was stirred for 3 hours. The reaction mixture thus obtained was poured into a mixture of ice and a 0.6 N diluted aqueous hydrochloric acid and the solid precipitated was collected by filtration. The solid thus obtained was washed sufficiently with water containing a small amount of ethanol on a filter funnel, and dried. The solid was dissolved in 150 ml. of hot benzene, and a small amount of the insoluble substances were removed by filtration, and then the filtrate was concentrated. The residue was dissolved in 20 ml. of ethyl acetate under heating, and 100 ml. of n-hexane was added thereto, and then cooled. The precipitate thus obtained was collected by filtration and dried. The yield was 28 g. (80% of the theoretical amount). m.p.: 241°–245° C.

The chemical structure of the products was determined from its IR spectrum, N.M.R. spectrum and Elementary analysis.

We claim:

1. A compound represented by the formula:

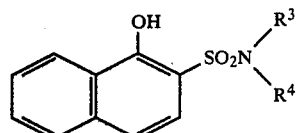

wherein $R^1$, $R^2$ $R^3$ and $R^4$, which may be the same or different, independently represent a hydrogen atom, a straight-chain alkyl group having 1 to 6 carbon atoms, a branched alkyl group having 3 to 6 carbon atoms or a cycloalkyl group having 5 to 6 carbon atoms or $R^1$ and $R^2$ may be connected with each other, together with the nitrogen atom, to form a

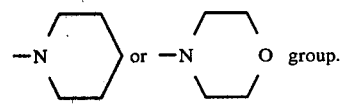

2. A compound as defined in claim 1 wherein $R^1$ and $R^2$ independently represent a hydrogen atom, a straight-chain alkyl group having 1 to 6 carbon atoms or a branched alkyl group having 3 to 6 carbon atoms, or a group together with the nitrogen atom, to form a

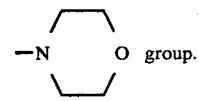

3. A compound as defined in claim 2 wherein $R^1$ and $R^2$ independently represent a hydrogen atom or methyl group, or a group together with the nitrogen atom, to form a

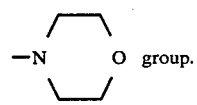

4. A compound as defined in claim 1 wherein $R^1$ and $R^2$ are the same.

5. A compound as defined in claim 4 wherein both $R^1$ and $R^2$ are methyl groups.

6. A compound as defined in claim 1 wherein $R^3$ and $R^4$ independently represent a hydrogen atom, a straight-chain alkyl group having 1 to 6 carbon atoms or a branched alkyl group having 3 to 6 carbon atoms.

7. A compound as defined in claim 6 wherein $R^3$ and $R^4$ independently represent a hydrogen atom, a straight-chain alkyl group having 1 to 4 carbon atoms or a branched alkyl group having 3 to 4 carbon atoms.

8. A compound as defined in claim 7 wherein the total sum of carbon atoms in both $R^3$ and $R^4$ is 4 to 6.

9. A compound as defined in claim 8 wherein $R^3$ is a hydrogen atom and $R^4$ is a tert-butyl group.

10. A compound as defined in claim 8 wherein both $R^3$ and $R^4$ are isopropyl groups.

11. A compound as defined in claim 3 wherein $R^3$ and $R^4$ independently represent a hydrogen atom, a straight-chain alkyl group having 1 to 4 carbon atoms or a branched alkyl group having 3 to 4 carbon atoms.

12. A compound as defined in claim 8 wherein both $R^1$ and $R^2$ are methyl groups.

* * * * *